United States Patent
Chaouk et al.

(10) Patent No.: US 9,581,835 B2
(45) Date of Patent: Feb. 28, 2017

(54) PATIENT INTERACTIVE FIT TOOL AND METHODOLOGY FOR CONTACT LENS FITTING

(71) Applicant: Johnson & Johnson Vision Care, Inc., Jacksonville, FL (US)

(72) Inventors: Hassan Chaouk, Jacksonville, FL (US); Thomas R. Karkkainen, Orange Park, FL (US); Kurt John Moody, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 78 days.

(21) Appl. No.: 14/291,339

(22) Filed: May 30, 2014

(65) Prior Publication Data

US 2015/0342453 A1 Dec. 3, 2015

(51) Int. Cl.
*A61B 3/02* (2006.01)
*G02C 7/04* (2006.01)
*G02C 7/02* (2006.01)
*A61B 3/028* (2006.01)

(52) U.S. Cl.
CPC .............. *G02C 7/047* (2013.01); *G02C 7/027* (2013.01); *A61B 3/028* (2013.01)

(58) Field of Classification Search
CPC ........... A61B 3/02; A61B 3/028; A61B 3/032; A61B 3/04; A61B 3/103; A61B 3/107; A61B 3/18; G02C 7/027
USPC ...... 351/223, 228, 237, 159.74, 159.77, 247
See application file for complete search history.

(56) References Cited

U.S. PATENT DOCUMENTS

| | | | |
|---|---|---|---|
| 4,979,812 A * | 12/1990 | Reese | A61B 3/02 351/203 |
| 7,914,148 B2 | 3/2011 | Fisher | |
| 8,047,652 B1 * | 11/2011 | Collazo | A61B 3/0033 351/223 |
| 8,393,733 B2 | 3/2013 | Wooley et al. | |
| 2008/0052194 A1 | 2/2008 | Shinohara | |
| 2010/0114540 A1 | 5/2010 | Shinohara | |
| 2012/0275677 A1 * | 11/2012 | Bower | G06F 19/321 382/131 |
| 2013/0201443 A1 * | 8/2013 | Back | G02C 7/041 351/159.08 |

(Continued)

FOREIGN PATENT DOCUMENTS

| | | |
|---|---|---|
| DE | 102009008876 A1 | 9/2010 |
| JP | 2009230699 A | 10/2009 |
| WO | WO2013140086 A1 | 9/2013 |

OTHER PUBLICATIONS

European Search Report for corresponding EPA No. 15169920.4 dated Sep. 18, 2015.

*Primary Examiner* — Huy K Mai
(74) *Attorney, Agent, or Firm* — Carl J. Evens (57) ABSTRACT

An interactive fit tool and methodology which may be utilized by an eye care professional to improve the efficiency and final outcome in selecting a pair of contact lenses targeted towards a specific patient visual need in the treatment of presbyopia. The interactive fit tool comprises an application which includes images that would allow a patient to decide if he or she desires balanced visual acuity, near biased visual acuity, or distance biased visual acuity. In addition, the interactive fit tool comprises fit guide tables and performs the calculations for vertex distance and spherical equivalent.

7 Claims, 4 Drawing Sheets

(56) References Cited

U.S. PATENT DOCUMENTS

| | | | |
|---|---|---|---|
| 2013/0201444 A1* | 8/2013 | Back | G02C 7/027 351/159.08 |
| 2013/0201447 A1* | 8/2013 | Thompson | A61B 3/02 351/201 |
| 2013/0253891 A1 | 9/2013 | Inoue | |
| 2014/0002799 A1* | 1/2014 | Wildsmith | A61B 3/00 351/223 |
| 2015/0049304 A1 | 2/2015 | Cussac | |

\* cited by examiner

PATIENT INTERACTIVE FIT TOOL AND METHODOLOGY FOR CONTACT LENS FITTING

BACKGROUND OF THE INVENTION

1. Field of the Invention

The present invention relates to fitting contact lenses on a patient for correcting presbyopia, and more particularly to a system and method for optimizing prescription selection based upon direct feedback from patients undergoing eye examinations and contact lens fitting utilizing a set of interactive simulations designed to demonstrate the impact of balancing near, intermediate and distance vision correction.

2. Discussion of the Related Art

As individuals age, their eyes are less able to accommodate, or bend their natural or crystalline lens, in order to focus on objects that are relatively near to the observer. This condition is known as presbyopia. More specifically, when an individual is born, the crystalline lens is pliable which makes it capable of a high degree of accommodation. As the individual ages, the crystalline lens gradually becomes more rigid and thus less able to accommodate. Similarly, for persons who have had their natural or crystalline lens removed and an intraocular lens or IOL inserted as a replacement, the ability to accommodate is absent. Although the intent of an accommodating IOL is to address this potential shortcoming, current accommodating IOL designs and concepts are relatively new and continue to evolve without providing a complete and satisfactory solution.

Among the methods used to correct for the eye's failure to accommodate is a method known as mono-vision in which, in most cases, a contact lens for correction of distance vision is utilized in the lens wearer's dominant eye, which is known to predominate for distance vision, coupled with a second contact lens for correction of near vision being utilized in the non-dominant eye. Mono-vision provides for both near and distance vision while allowing the brain to compensate as how the images should be construed. Mono-vision has limitations secondary to a decrease in binocularity. Another known method for correction of presbyopia is to use bifocal or multifocal contact lenses in both of the individual's eyes. There are many forms of bi-focal or multi-focal contact lenses for the correction of presbyopia. These design forms include concentric rings and aspheric designs, both of which may be designed for center distance or center near. All of these designs function by providing a range of powers within the pupil of the eye. For example, a concentric ring design may have a central ring that provides powers that are nominally equal to the power required to correct the distance vision of the subject, an adjacent ring that provides near powers, and an outer ring that also provides distance powers. There may also be fitting strategies to address intermediate vision demands between near and far distances, for example, computer screen viewing. Use of bifocal or multifocal lenses in both eyes results in a reduction of image contrast and resolution compared to mono-vision but usually maintains binocularity. Yet another method of treating presbyopia is to place a bifocal or multifocal lens in one eye and a single vision lens in the other eye. The disadvantage in using this method is in the large number of lenses that must be considered in order to provide the individual with satisfactory lens performance and the limitation of binocularity at near distance.

As may be seen from above, there are numerous solutions for the treatment of presbyopia and no single concept may be ideal for all individuals. Fit guides and tools are available to eye care specialists/professionals to help in selecting a starting pair of contact lenses. Some of these tools also help with more complicated calculations such as vertex distance and spherical equivalent, but none have a patient interactive segment that would allow a patient to see a simulation of what the contact lens solution could provide to them. Accordingly, there exists a need for an interactive fit tool that would allow an individual to be able to get a sense of what their vision would be like under real world circumstances and to select a desired visual experience prior to being fitted with a set of contact lenses.

SUMMARY OF THE INVENTION

The interactive fit tool of the present invention overcomes the deficiencies associated with the contact lens fitting process for individuals with presbyopia as briefly described above.

In accordance with one aspect, the present invention is directed to an interactive fit tool for individuals with presbyopia based upon refraction and eye dominance data along with patient feedback on preferred vision. The interactive fit tool comprises a collection of images which demonstrate a range in visual quality over a range of distances, multiple fit guides each comprising suggested contact lens pairs based upon patient need and patient preference, the multiple fit guides coordinated to the collection of images, and a means for calculating vertex distance and the spherical equivalent for a patient.

In accordance with another aspect, the present invention is directed to a method for optimizing contact lens selection for individuals with presbyopia based upon refraction and eye dominance data along with patient feedback on preferred vision. The method comprises the steps of presenting a collection of images which demonstrate a range in visual quality over a range of distances to a patient, selecting a set of contact lenses from a fit guide based upon the best spherical equivalent refraction and ADD power for both eyes of the patient based upon patient preferences as determined from the collection of images, assessing the patient's vision, and repeating the process until the patient's vision is acceptable to the patient.

The interactive fit tool of the present invention allows an individual who has undergone a comprehensive subjective refraction and has an interest in multifocal contact lenses, and more particularly, multifocal soft contact lenses to view a series of images that would simulate the type of distance, intermediate and near vision that a specific pair of trial lenses would result in or provide. This process would assist the contact lens fitter, i.e. eye care professional, to select a pair of lenses that would be best aligned with the patient's specific vision needs and preferences and give the patient an appropriate expectation of the vision they could expect/realize with this technology. More particularly, this process preferably saves the individual from trying on lenses for a given period of time and potentially exchanging them for a different pair when the results are not as expected. Additionally, the process would also complete the complicated calculations of vertex distance and spherical equivalent that may be sources of additional error during the fitting process.

The images in conjunction with the data or information collected during the refraction will allow the individual to experience the visual acuity offered by the various lenses or lens solutions without leaving the eye care professional's office and thus start out with the best lenses for that individual based upon their individual preferences.

More specifically, a patient that has an interest in contact lenses or one that currently wears contact lenses but would prefer a better prescription would undergo an examination including a comprehensive subjective refraction which includes sphere, cylinder, axis, add power and eye dominance. The data collected from the examination would be input into the interactive fit tool of the present invention. The patient would then put on a correction (either their own or a trial lens correction) that would allow them good near correction to view a number of simulations of the type of vision that may be expected with a given contact lens solution. One simulation or scene may illustrate substantially equal visual acuity for near, intermediate and distance. A second simulation or scene may illustrate enhanced visual acuity for distance, lessened visual acuity for near, and something in between for intermediate. A third simulation or scene may illustrate enhanced visual acuity for near, lessened visual acuity for distance, and something in between for intermediate. The patient would be afforded the opportunity to select the type of vision that they feel would best suit their daily needs. The results of the patient's selection would be entered into the interactive fit tool whereupon it would be integrated into an associated fit guide that would factor in the patient's visual simulation selection along with any of the calculations that would be needed for vertex distance and spherical equivalence along with the current product offerings of a contact lens company, wherein the output would be a suggested starting pair of contact lenses for the patient. It is important to note that the simulations or scenes may be separate images or a single image having zones within the image representing the different simulations described above.

The present invention is unique in that it incorporates into the lens fitting and selection procedure the patients input of what level of vision is needed for their particular daily lives. The result of this would make the lens selection process more efficient by eliminating unnecessary trial fits and would give the patient a more realistic expectation in regard to the level of vision they could expect by a contact lens solution. This in turn would be beneficial to the contact lens fitter in that less total chair time would be needed to achieve a successful fit, particularly if additional visits were reduced and or eliminated. For some patients the possible solutions may not meet their needs thus by using this invention it would eliminate unnecessary lens fits and allow the patient to evaluate other forms of vision correction.

The interactive fit tool of the present invention may be implemented in any number of ways, for example, as an application that may be utilized on a personal computer, tablet or even a cell phone. The interactive fit tool offers a simple and effective means for fitting patients with presbyopia.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Contact lenses or contacts are simply lenses placed on the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow substantial oxygen transmission through the contact lens to the cornea which potentially could cause a number of adverse clinical effects. The rigid contact lenses of the past have undergone vast improvements in regard to oxygen transmission secondary to newer semi-flexible materials and thus a significant improvement in corneal health. These contact lenses still have limited use due to initial comfort that may be marginal at best. Later developments in the field gave rise to soft contact lenses, based upon hydrogel materials, which have become extremely popular and widely utilized today. Most recently, silicone hydrogel contact lenses that are available today combine the benefit of silicone, which has higher oxygen permeability, with the proven comfort and clinical performance of hydrogels. Essentially, these silicone hydrogel based contact lenses have higher oxygen permeability and are generally more comfortable to wear than the contact lenses made of the earlier hard materials. However, these new contact lenses are not totally without limitations.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia i.e. the loss of the ability of the crystalline lens to accommodate. Contact lenses are available in a variety of forms and are made of a variety of materials to provide different functionality. Daily wear soft contact lenses are typically made from soft polymer-plastic materials combined with water for oxygen permeability. Daily wear soft contact lenses may be daily disposable or extended wear disposable.

Daily disposable contact lenses are usually worn for a single day and then thrown away, while extended wear disposable contact lenses are usually worn for a period of up to thirty days. Colored soft contact lenses use tinting processes to provide different functionality. For example, a visibility tint contact lens uses a light tint to aid the wearer in locating a dropped contact lens. Eye enhancement contact lenses use either translucent or opaque tints to enhance or alter the appearance of one's eyes for a cosmetic benefit. Rigid gas permeable hard contact lenses are made from silicone polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

Presbyopia is corrected by algebraically adding plus optical power to a portion of the optical zone of lenses to correct the wearer's or patients near visual acuity requirements. There are many forms of bi-focal or multi-focal contact lenses for the correction of presbyopia. These design forms include concentric rings and aspheric designs, both of which may be designed for center distance or center near. All of these designs function by providing a range of powers within the pupil of the eye. For example, a concentric ring design may have a central ring that provides powers that are nominally equal to the power required to correct the distance vision of an individual, an adjacent ring that provides near power, and an outer ring that provides distance power. In accordance with the present invention, improved performance and reduced fitting time may be achieved by utilizing lens pairs that act synergistically to provide the lens wearer with good binocularity and consistent performance in near, intermediate and distance vision.

As set forth above, any number of contact lens designs may be utilized for the correction of presbyopia. In accordance with one exemplary embodiment, as disclosed in U.S. Pat. No. 8,393,733 assigned to Johnson & Johnson Vision Care Inc., sets of contact lenses satisfying certain design constraints are disclosed for treating presbyopia. Each of the sets of lenses comprises multiple lenses that provide sphere power and add power over desired ranges in a multifocal design. Preferably, each set comprises multiple lenses that provide sphere power over the range of −12.00 to +8.00 diopters in 0.5 diopter increments and add power over the range of 0.75 to 2.50 diopters in increments of 0.25 diopters. More preferably, one set of lenses provides sphere power over the range of −12.00 to +8.00 diopters in 0.50 diopter increments and add power over the range of 0.75 to 1.75 diopters in increments of 0.25 diopters, a second set of lenses provides sphere power over the range of −12.00 to +8.00 diopters in 0.5 diopter increments and add power over the range of 0.75 to 2.50 diopters in increments of 0.25 diopters, and a third set of lenses provides sphere power over the range of −12.00 to +8.00 diopters in 0.50 diopter increments and add power over the range of 1.25 to 2.50 diopters in increments of 0.25 diopters. These lenses may be organized into the pair combinations set forth in Tables 1 through 3 given below. A detailed description of the meaning and use of these tables is given subsequently. The tables may be incorporated into the interactive fit tool of the present invention along with the exemplary simulations described subsequently. However, it is important to note that any other similar tables may be utilized.

TABLE 1

| | Patient Need Balance Approach | | | | | | | |
|---|---|---|---|---|---|---|---|---|
| EYE | +0.75 D | +1.00 D | +1.25 D | +1.50 D | +1.75 D | +2.00 D | +2.25 D | +2.50 D |
| DOMINANT EYE | LOW | LOW | LOW | MID | MID | MID | MID | MID |
| NON-DOMINANT EYE | LOW | LOW | LOW | MID | MID | HIGH | HIGH | HIGH |

TABLE 2

| | Patient Need Distanced Optimized Approach | | | | | | | |
|---|---|---|---|---|---|---|---|---|
| EYE | +0.75 D | +1.00 D | +1.25 D | +1.50 D | +1.75 D | +2.00 D | +2.25 D | +2.50 D |
| DOMINANT EYE | Acuvue ® Moist ® | Acuvue ® Moist ® | Acuvue ® Moist ® | LOW | LOW | MID | MID | MID |
| NON-DOMINANT EYE | LOW | LOW | LOW | MID | MID | MID+ | MID+ | MID+ |

TABLE 3

| | Patient Need Near Optimized Approach | | | | | | | |
|---|---|---|---|---|---|---|---|---|
| EYE | +0.75 D | +1.00 D | +1.25 D | +1.50 D | +1.75 D | +2.00 D | +2.25 D | +2.50 D |
| DOMINANT EYE | LOW | LOW | LOW | MID | MID | MID | MID | MID |
| NON-DOMINANT EYE | LOW+ | LOW+ | LOW+ | MID+ | MID+ | HIGH+ | HIGH+ | HIGH+ |

The interactive fit tool of the present invention allows a patient that has an interest in a multifocal contact lens to view a series of images that would simulate the type of distance, intermediate and near vision that a specific pair of trial lenses would result in. The patient would undergo an examination first, including a comprehensive subjective refraction which includes sphere, cylinder, axis, add power and eye dominance. The data collected from the examination would be input into the interactive fit tool. The patient would then put on their current prescription lenses and view a number of simulations of the vision that may be expected with a given contact lens solution, which preferably is a lens pair from the lenses described above. In addition, the fitting process would also preferably automatically complete the complicated calculation of vertex distance, i.e. a calculation that would determine the needed corneal power that would be required based on the lens value determined in a trial frame or phoropter, typically a 12 mm distance from the cornea, and the spherical equivalent, i.e. the spherical power factor required to compensate for cylindrical error, which may be a source of error during the fitting process.

Figure 1:
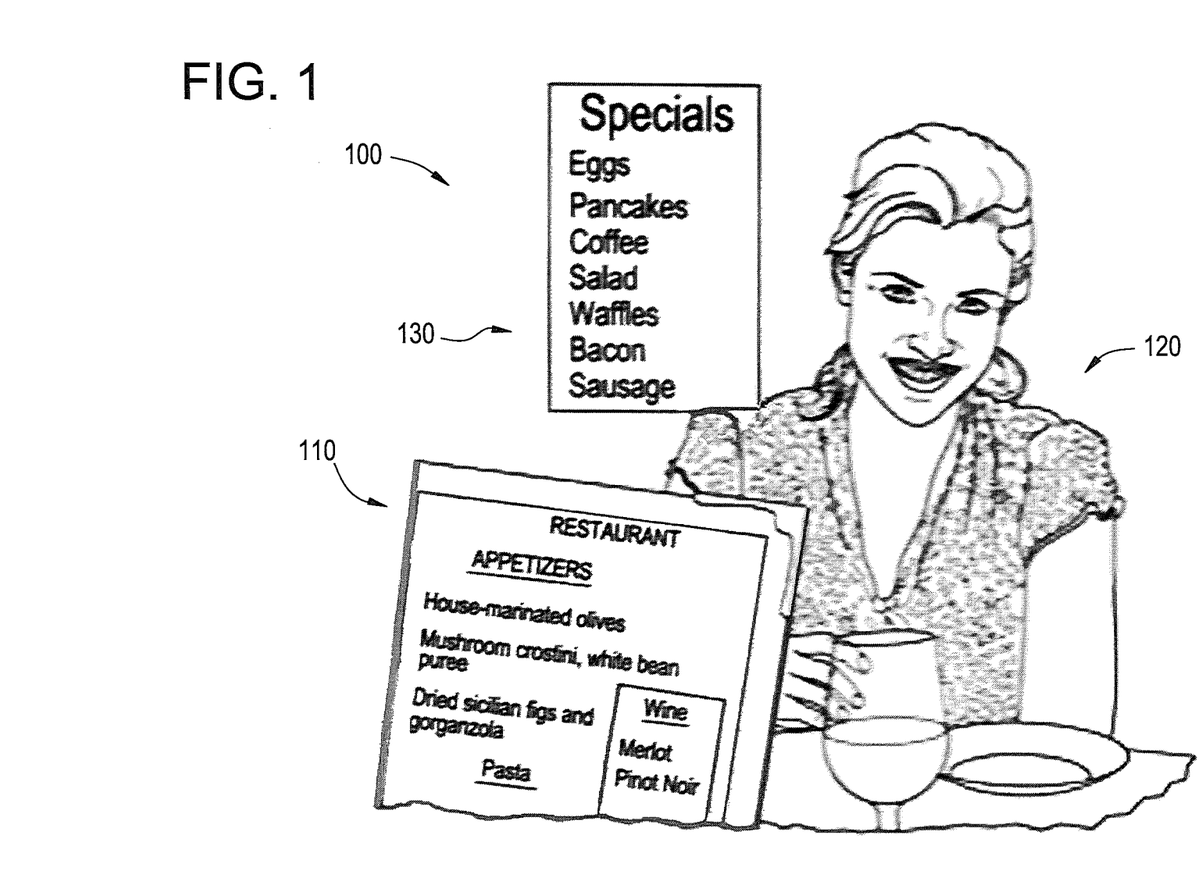
FIG. 1 is an illustration of a first scene with a balanced view in accordance with the present invention.
Figure 2:
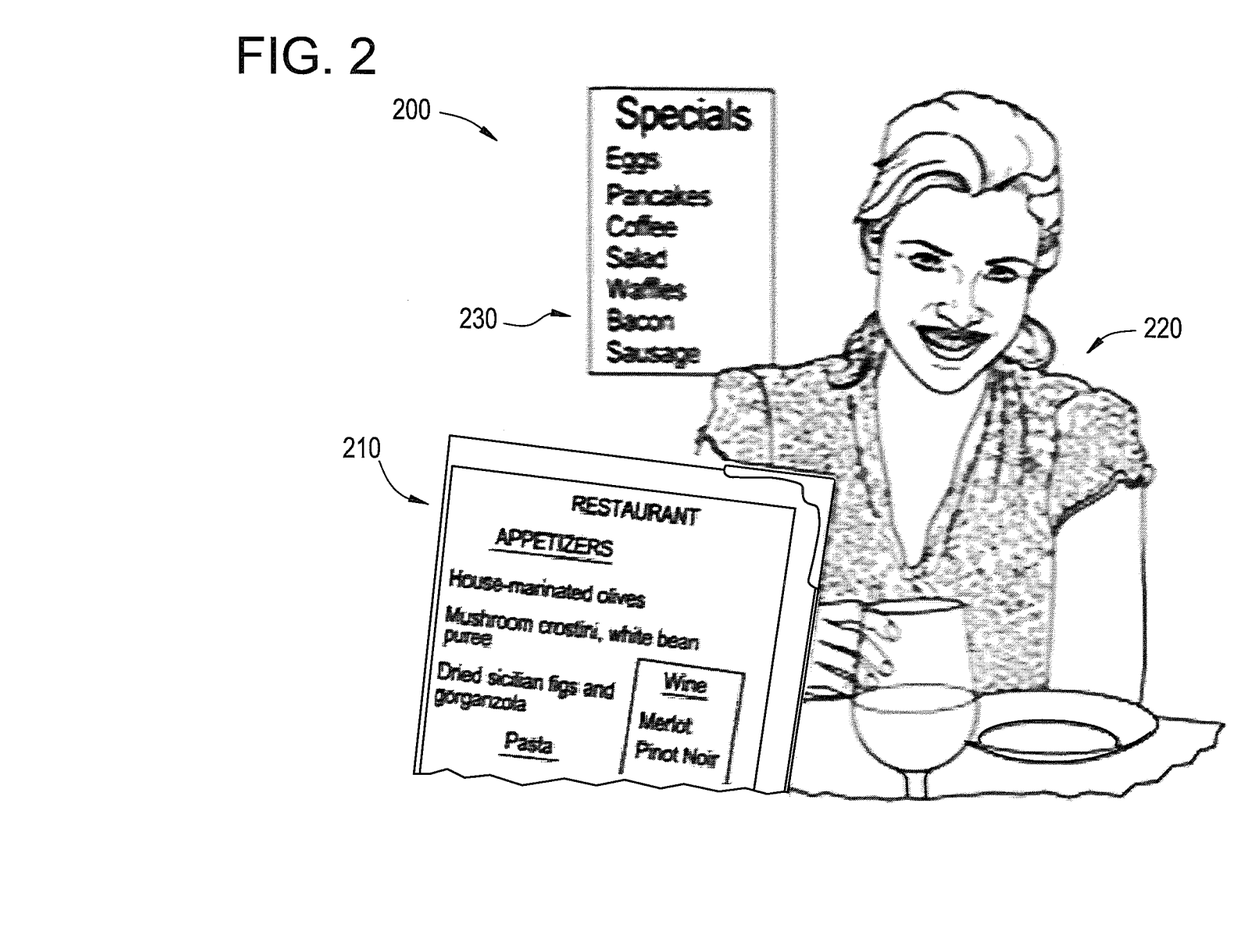
FIG. 2 is an illustration of a second scene with a distance optimized view in accordance with the present invention.
Figure 3:
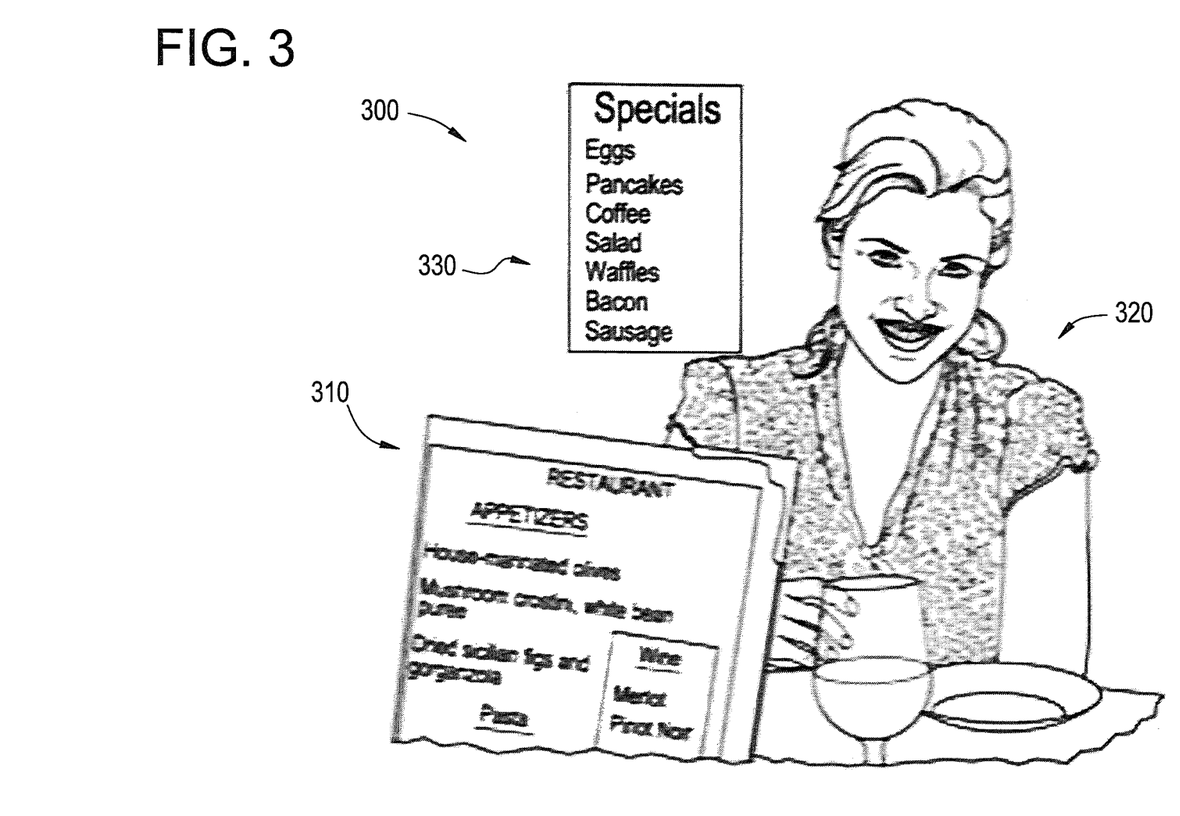
FIG. 3 is an illustration of a third scene with a near optimized view in accordance with the present invention.

In accordance with one exemplary embodiment, a first simulation (balanced) comprising an image is presented to the patient and illustrates substantially equal visual acuity for near, intermediate and distance. It is important to note that this does not mean one hundred (100) percent for each viewing distance, but rather approximately seventy (70) percent for each of the three viewing distances. Referring now to FIG. 1, there is illustrated the first simulation 100. As shown, the near 110, intermediate 120, and distance region 130 represented in the image are balanced in terms of visual acuity. A second simulation (distance optimized) comprising an image is then presented to the patient and illustrates enhanced visual acuity for distance, for example, approximately ninety (90) percent visual acuity, lessened visual acuity for near, for example, approximately fifty (50) percent visual acuity, and something in between for intermediate, for example, seventy (70) percent visual acuity. Referring now to FIG. 2, there is illustrated the first simulation 200. As shown, the near 210, intermediate 220, and distance region 230 represented in the image are not balanced in terms of visual acuity. The distance region 230 is clear, the near region 210 is blurry and the intermediate region 220 is less clear than the distance region 230. A third simulation (near optimized) comprising an image is then presented to the patient and illustrates enhanced visual acuity for near, for example, approximately ninety (90) percent visual acuity, lessened visual acuity for distance, for example, approximately fifty (50) percent visual acuity, and something in between for intermediate, for example, seventy (70) percent visual acuity. Referring now to FIG. 3, there is illustrated the first simulation 300. As shown, the near 310, intermediate 320, and distance region 330 represented in the image are not balanced in terms of visual acuity. The distance region 330 is blurry, the near region 310 is clear and the intermediate region 320 is less clear than the near region 310. As it is impossible to provide one hundred percent visual acuity at all distances without the use of adaptive or dynamic optics, the percentages given above represent the relative visual acuity at the three distances. Although described herein, it is worth noting that any selection is a balancing of needs and preferences. Once shown the three simulations, the patient would decide which best suits his or her requirements and the appropriate lens pair, for example, from those described above may be selected. Essentially, the results of the interactive fit tool information would integrate into an associated fit guide that would factor in the patient's visual simulation selection along with any of the calculations that would be needed for vertex distance and spherical equivalence based upon the comprehensive eye examination along with the current product offerings of a contact lens company.

Although shown and described are three simulations, it is important to note that other suitable combinations may be utilized in accordance with the present invention. For example, the simulations may represent near and intermediate, intermediate and distance, near and far as well as images under different light settings. The more light present, the easier it is for an individual with presbyopia to focus on near objects. In addition, the images may be two-dimensional as illustrated or three-dimensional.

It is important to note that the simulations or scenes may be separate image or a single image having zones within the image for the different simulations described above. The simulations may be as simple as graphic images or photographic images, or preferably as images presented on an electronic device such as a personal computer, tablet or cell phone. In a preferred exemplary embodiment, the simulations or scenes would along with the contact lens tables described above be incorporated into one single interactive fit tool application that also implements all the calculations described above.

In accordance with the present invention, if the patient selects the first simulation or scene; namely, substantially equal visual acuity for near, intermediate and distance (balanced), a first lens set of multi-focal lenses from the lenses in Table 1 is selected based on the best spherical equivalent refraction and ADD power for both eyes. After the contact lenses have settled on the patient's eyes, for example, after ten (10) minutes or so, the patient's vision is assessed at both distance and near. If the patient's vision is acceptable, the eye care professional continues with the fit assessment and dispensing of the prescription as per standard protocol. If the patient's vision is not acceptable, the eye care professional should ensure that the proper initial lens power was selected by performing a distance over-refraction with +/−0.25 D trial lenses or flippers to determine if a change in the initial lens power is required. The over-refraction should preferably be performed outside of the phoropter under normal room illumination. The patient should be rechecked for both distance and near visual acuity with the over-refraction in place. If a change is indicated, then that particular set of contact lenses should be dispensed and evaluated as described herein. If a change in the initial lens power is not helpful, then it should be determined if the patient would need better near or distance vision. Based on this information, the interactive fit tool would be utilized to determine a new set of contact lenses and the assessment would be repeated by the eye care professional. For example, if it is determined that the patient desires or requires improved distance vision, than a contact lens set from Table 2 may be selected. Alternatively, if it is determined that the patient desires or requires improved near vision, than a contact lens set from Table 3 may be selected.

The interactive fit tool of the present invention is simply a tool to aid the eye care professional. The eye care professional must still utilize his or her professional judgment in determining a particular prescription.

It is important to note the differences in the three tables. Specifically, the + sign following the LOW, MID or HIGH is an indication for the eye care professional to add +0.25 D to the distance contact lens power on the non-dominant eye as is explained in more detail subsequently. In addition, the Acuvue® Moist® brand contact lenses referenced in Table 2 are non-multifocal contact lenses with no ADD power. If these lenses or similar lenses in terms of intended function from another company are selected, then this is a form of modified mono-vision. More specifically, this pair combination offers a straight or simple distance correction lens in the dominant eye and a multifocal correction lens in the non-dominant eye. The Acuvue® Moist® brand contact lenses are a product of Johnson & Johnson Vision Care Inc.

In order to illustrate the +0.25 D add described above, a simple example is given. In this example, the patient requires a +1.75 D ADD and has a near complaint. Referring to Table 3 (near complaint), under the +1.75 D ADD it indicates to maintain the dominant eye at MID and add +0.25 D to the non-dominant eye; namely, MID+. Using actual numbers, if the patient has a spherical equivalent distance refraction of OD: −2.50 D and OS: −3.00 D (non-dominant eye), the new lens pair selected from Table 3 would be OD: −2.50 MID ADD and OS: −2.75 MID ADD.

By utilizing the interactive fit tool of the present invention, the time to fit a patient is greatly reduced because he or she is shown what their vision may look like without having to actually wear a set of contact lenses, hence a simulation. The patient would have an opportunity to experience the expected visual outcome of a given set of contact lenses without actually wearing them, thus setting expectations and filtering through options via the simulation provided by the interactive fit tool. The interactive fit tool preferably comprises the simulations, fit guides for a number of contact lens manufacturers, and the software to input the data collected and perform the necessary calculations described herein.

Figure 4:
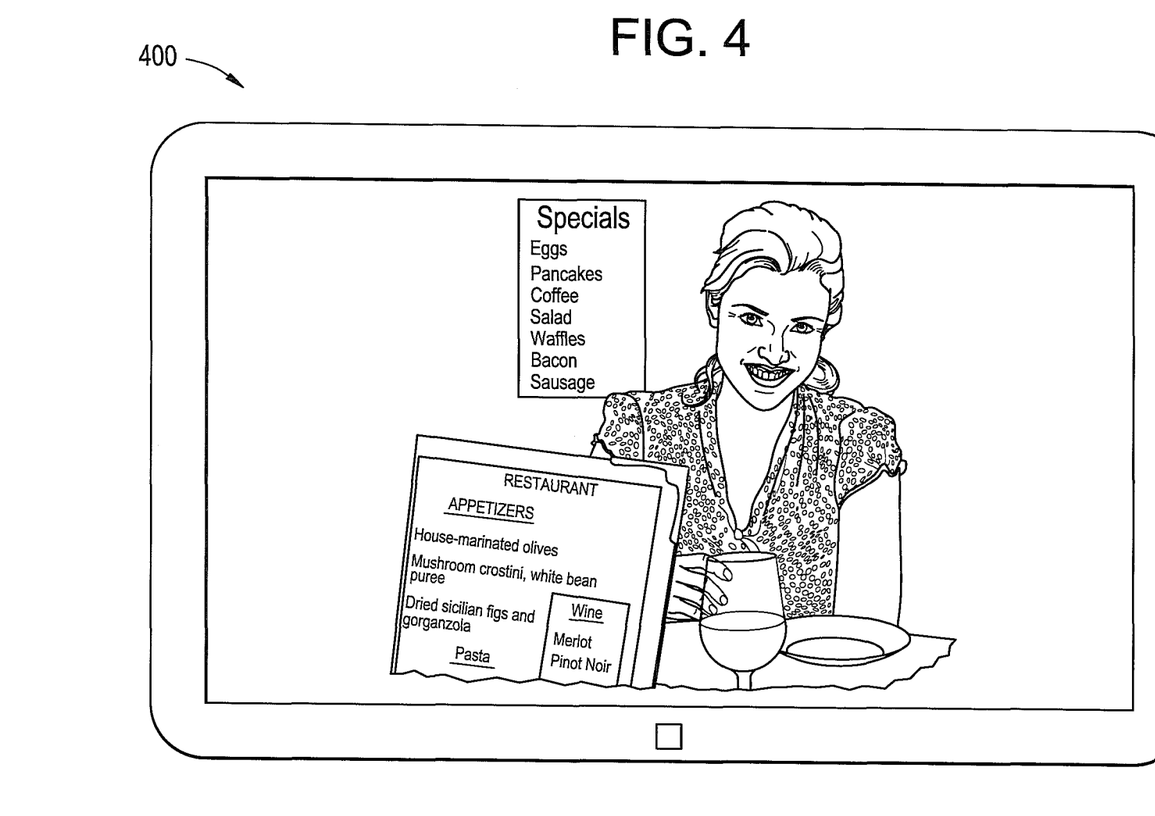
FIG. 4 is a diagrammatic representation of an interactive fit tool in accordance with the present invention.

The calculations themselves are known, but are fully automated in the interactive fit tool further expediting the fitting process and reducing not only the time involved but the risk of error as well. As set forth above, the interactive fit tool may be implemented in any suitable manner. FIG. 4 illustrates a simple electronic device, for example a lap top computer or any other suitable mobile device with a means for processing data, making calculations and storing images as well as data on which the interactive fit tool may be implemented. The electronic device also preferably comprises a display for displaying the scenes as well as the data collected and the results of various calculations. The electronic device may be configured as a touch screen device, a keyboard entry device, and/or a voice activated device. The interactive fit tool may be implemented as an application which may run on a smart phone. The electronic device 400 is configured to display images, accept data, present data, and make real time calculations.

The fitting tool and process may be utilized at any time the patient desires, for example, at his or her annual check-up or at any time he or she feels a change may be necessary.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An interactive fit tool for optimizing contact lens selection for individuals with presbyopia based upon refraction and eye dominance data along with patient feedback on preferred vision, the fit tool comprising:

a collection of images, each including a single scene composed of elements that demonstrates a range in visual quality over a range of distances to be presented to a patient as a single scene, wherein the collection of images comprises a first scene illustrating substantially equal visual acuity for near, intermediate and distance such that all elements appear in equal focus, a second scene illustrating enhanced visual acuity for distance, lessened visual acuity for near and a visual acuity between the distance and near for intermediate such that the near elements are less in focus than the distance elements, and a third scene illustrating enhanced visual acuity for near, lessened visual acuity for distance and a visual acuity between the near and distance for intermediate such that the near elements are more in focus than the distance elements, the first, second and third scenes being presented one at a time for viewing by a patient with both eyes seeing the same image;

multiple fit guides each comprising suggested contact lens pairs based upon patient need and patient preference, the multiple fit guides coordinated to the collection of images, wherein each comprise pairs of contact lenses having a range of powers and ADD values that provide vision correction corresponding to the preference for one of the first, second and third scenes; and a means for calculating vertex distance and the spherical equivalent for a patient.

2. The interactive fit tool according to claim 1, further comprising an electronic device having a data processor for making calculations, memory for storing data and images, and a means for data entry and display.

3. The interactive fit tool according to claim 2, wherein the means for calculating vertex distance and the spherical equivalent for a patient comprises an algorithm implemented via the data processor.

4. The interactive fit tool according to claim 2, wherein the electronic device comprises a lap top computer.

5. The interactive fit tool according to claim 2, wherein the electronic device comprises a tablet.

6. The interactive fit tool according to claim 2, wherein the electronic device comprises a smart phone.

7. A method for optimizing contact lens selection for individuals with presbyopia based upon refraction and eye dominance data along with patient feedback on preferred vision, the method comprising the steps of:

(a) presenting a collection of images which demonstrate a range in visual quality over a range of distances to a patient, each including a single scene composed of elements that demonstrates a range in visual quality over a range of distances to be presented to a patient as a single scene, wherein the collection of images comprises a first scene illustrating substantially equal visual acuity for near, intermediate and distance such that all elements appear in equal focus, a second scene illustrating enhanced visual acuity for distance, lessened visual acuity for near and a visual acuity between the distance and near for intermediate such that the near elements are less in focus than the distance elements, and a third scene illustrating enhanced visual acuity for near, lessened visual acuity for distance and a visual acuity between the near and distance for intermediate such that the near elements are more in focus than the distance elements, the first, second and third scenes being presented one at a time for viewing by a patient with both eyes seeing the same image;

(b) selecting a set of contact lenses from a fit guide based upon the best spherical equivalent refraction and ADD power for both eyes of the patient based upon patient preferences as determined from the collection of images;

(c) assessing the patient's vision; and (d) repeating steps a-c until the patient's vision is acceptable to the patient.

* * * * *